United States Patent [19]

Shippert

[11] 4,274,402
[45] Jun. 23, 1981

[54] NOSE SPLINT

[75] Inventor: Ronald D. Shippert, Englewood, Colo.

[73] Assignee: The Denver Splint Company, Littleton, Colo.

[21] Appl. No.: 35,918

[22] Filed: May 3, 1979

[51] Int. Cl.³ .............................................. A61F 5/04
[52] U.S. Cl. .................................. 128/89 R; 128/76 C
[58] Field of Search ................. 128/89 R, 76 C, 87 R, 128/155

[56] References Cited

U.S. PATENT DOCUMENTS

| 2,933,083 | 4/1960 | Kozdas | 128/89 R |
| 3,046,989 | 7/1962 | Hill | 128/348 |
| 3,426,751 | 2/1969 | Radewan | 128/76 C |
| 3,971,374 | 7/1976 | Wagner | 128/155 |

OTHER PUBLICATIONS

Alumafoam Nasal Splint, Conco Catalogue, p. 12, Oct. 1972.

Primary Examiner—John D. Yasko
Attorney, Agent, or Firm—Sheridan, Ross, Fields & McIntosh

[57] ABSTRACT

A nose splint is provided which has a resilient layer having an adhesive coating on one side and a malleable metal layer permanently attached to the opposite side. The splint is applied after a traumatized nose has been taped with adhesive tape by applying the adhesive surface of the splint to the bridge of the nose and forming the splint around the nose so as to press any edema fluid between the incised skin and the bone and cartilage out of this area so that the skin tightly engages the bone and cartilage and is held thereagainst by adhesive contact with both the incised area and the untreated area so as to minimize swelling of the tissue and separation of the tissue from the bone and cartilage during the initial healing process.

4 Claims, 8 Drawing Figures

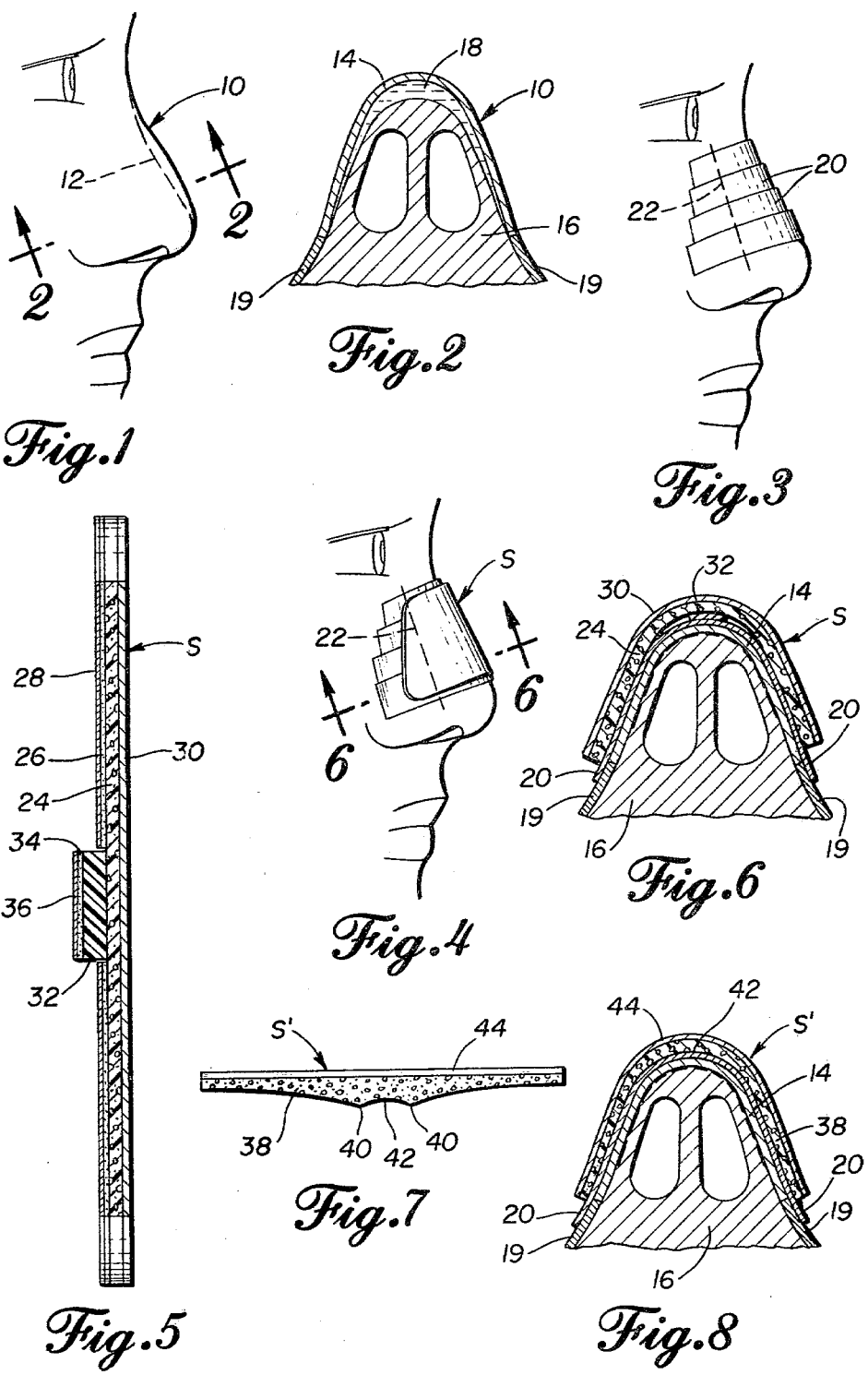

NOSE SPLINT

DESCRIPTION

1. Technical Field

This application is related to my co-pending application Ser. No. 813,800, filed July 8, 1977, now U.S. Pat. No. 4,153,051. The device of this invention lies in the field of splints or braces for application to traumatized portions of a human body and is directed more particularly to a device of this class which is useful in maintaining during the healing period a traumatized nose resulting from injury or surgery in the desired size and shape after squeezing out all of the edema fluid from the soft tissue.

2. Background Art

For many years it has been common practice to form splints from Plaster of Paris for use in maintaining immobility of bony segments after surgery. They are difficult to make and difficult to retain in place, requiring excessive taping or bandaging, in addition to being uncomfortable and unsightly. Various other approaches have been tried with indifferent success.

One approach has been the molding of a complete face mask, the nose portion of which is then modified to the desired contour. One or more blanks of sheet material are then formed to fit the contour and secured to a restraining member. The device is placed over the nose and an elastic band connected to the ends of the restraining member is passed around the back of the head to hold the splint in place. An example of this type is disclosed in U.S. Pat. No. 3,742,943 to Malmin. Obviously the method is expensive and time consuming and the splint is easily displaced from its intended position.

In a somewhat similar approach a piece of malleable sheet metal of about the same area as the nose is laid against the nose and then pressed inward to assume the same shape as the nose. A retainer similar to a pair of goggles is applied to the splint and a headband connected to the ends of the retainer tends to hold it in place. An example of this type is disclosed in U.S. Pat. No. 3,835,848 to Berner. While the method of manufacture is simpler and cheaper than that of Malmin, it suffers from the same disadvantages in use. The device is uncomfortable and unsightly and the splint itself is easily displaced especially when the wearer is sleeping. Since neither of these devices is directly secured to the nose, they both fail to maintain constant pressure on precise areas to prevent swelling or distortion.

Perhaps the most common nose splint is one made of maleable sheet metal which is bent to conform to the desired shape of the nose and is held in place by strips of adhesive tape extending across the splint and the malor emenences. However, without adhesion between the splint and nose, the splint does little to prevent the build up of edema fluid between incised tissue and the bony structure of the nose.

DISCLOSURE OF INVENTION

The device of this invention and its method of application overcome the difficulties and disadvantages mentioned above and provide a compound splint which is inexpensive in materials, easy to apply and form to the desired shape, and firmly anchored in position to perform its proper function.

Generally stated, the total compound splint includes a resilient support layer having an adhesive surface on one side and a malleable restraining component attached directly to the other side of the support layer. Underlying the splint is a base layer which may be a single piece of adhesive tape but preferably consists of a plurality of narrow strips of tape laid across the nose laterally with each successive strip overlapping the preceding one in the longitudinal direction and firmly pressed in place. The support layer of the splint has a first-adhesive side or face adapted to engage and adhere to the tape on the nose.

More particularly, the invention contemplates a nose splint and a method of applying the same which greatly minimizes the possibility of swelling due to edema fluid and blood building up in the area between the bone or cartilage and the incised skin over the nose to avoid possible splaying of the bone and the creation of a nose sometimes known as a "parrot nose" or "polly nose." The nose splint is formed as a unitary structure having a foam layer formed with an adhesive surface on one side and a contiguous permanently attached malleable aluminum metallic layer on the other side. The foam is thicker at the center of the splint than at the edges and the adhesive may be covered with a protective paper backing prior to use.

Successive strips of adhesive tape are placed across the bridge of the nose over the incised area and extend back onto untreated adjacent skin area. In order to hold or press the incised skin firmly against the underlying bone and cartilage to keep the edema fluid out of this area so that proper healing can take place, the nose splint of this invention can be used. The wider central foam portion of the splint is placed over the bridge of the nose and the splint is bent around to conform in shape to the nose and the adhesive surface of the foam adheres tightly to the adhesive both over the incised area and also it extends outwardly beyond this incised area to untreated skin. Because of the adhesive contact between the foam of the splint and the tape over the nose, the possibility of the incised skin stretching due to edema fluid is reduced, and thereby better contact is maintained between the incised skin and the bone and cartilage structure of the nose to enhance proper healing.

In one embodiment, a separate foam strip is attached to the central portion of the principal foam layer to provide increased thickness at the center. Both the foam layer and the foam strip have an adhesive surface which may be covered by a protective paper covering prior to use.

In a second embodiment the foam layer is tapered outwardly from the center and has a pair of spaced parallel ribs along the center with a trough therebetween which conforms with the shape of the bridge of the nose.

Thus, a nose splint has been provided and a method for applying the same wherein it forms a relatively rigid protection for the nose and adhesively adheres to the incised skin area as well as untreated skin area to minimize swelling of the incised area to promote better healing.

BRIEF DESCRIPTION OF THE DRAWINGS

Additional advantages and novel features of the invention will become apparent from the description which follows in conjunction with the accompanying drawings in which:

FIG. 1 is a fragmentary side elevation of an individual having a "parrot nose" as may result in prior art treatment, the proper nose form being shown in dotted lines;

FIG. 2 is an enlarged section, taken along line 2—2 of FIG. 1, showing edema fluid between the incised skin and the bone and cartilage structure in the nose;

FIG. 3 is a fragmentary side elevational view of an individual with strips of adhesive tape attached across the nose preparatory to using the nose splint of this invention;

FIG. 4 is a fragmentary side elevation, similar to FIG. 3, but showing the nose splint of this invention in place;

FIG. 5 is an enlarged section through one form of the nose splint of this invention;

FIG. 6 is a section, taken along line 6—6 of FIG. 4, showing how the nose splint of this invention holds the incised skin against the bone and cartilage and minimizes any stretching of the incised skin area during healing;

FIG. 7 is a side elevation of an alternative nose splint constructed in accordance with this invention;

FIG. 8 is a section through a nose showing the nose splint of FIG. 7 in place.

BEST MODE FOR CARRYING OUT THE INVENTION

In the post-operative treatment of a patient who has had nose surgery, it is extremely important that the incised tissue be held tightly against the cartilage and bone structure of the nose during the initial healing process. Should this not occur, the individual may end up with a nose which is commonly referred to as a "parrot nose" or a "polly nose" as illustrated by nose 10 in FIG. 1. The normal nose would follow along dotted line 12. The cause of the "polly nose" can best be understood by referring to FIG. 2 in which such a nose is shown in section. During surgery, the gristle and bone in the nose is cut by making an incision through the nostril and then the skin 14 over the bridge of the nose is incised or cut from the underlying gristle and bone 16. After surgery, the space between skin 14 and bone 16 fills up with blood and edema fluid 18 whereas the untreated skin 19 at the rear portion of the nose is still attached to the bone and no fluid forms in this area.

If nothing is done to prevent edema fluid 18 from entering the space between skin 14 and bone 16, the skin 14 will be stretched and held away from the bone by the fluid. This fluid then remains in the incised area and may eventually form scar tissue in an irregular pattern joining the skin 14 to the bone 16 at different points. This can result in a pock marked nose which is unsightly and also one which has a bulbous or parrot nose appearance as shown in FIG. 1.

Therefore, after nose surgery precautions are made to minimize the possibility of edema fluid forming between incised skin 14 and the bone 16. In particular, the first post operative treatment is to apply strips of adhesive tape 20 across the bridge of the nose which each extend across the incised area indicated by dotted line 22. The edema fluid is squeezed out from between the incised tissue 14 and the bone 16 as the tape strips are applied. With most prior art devices these tape strips are the main restraining force to prevent swelling and to prevent the edema fluid from reentering the space between the incised tissue 14 and bone 16.

The novel nose splint S of this invention, like prior art nose splints, protects the nose should it be bumped during the healing process, but unlike other nose splints has a second function of cooperating with the tape strips 20 to minimize swelling of incised tissue 14 and the filling of the space between that tissue and bone 16 with edema fluid 18.

As best seen in FIG. 5, nose splint S comprises a resilient layer 24 of foam material such as polyurethane or it could be a sialastic material. The foam has an adhesive coating 26 on one side which is conveniently protected by a paper layer 28 prior to use. Permanently attached to the other side is a malleable metal layer 30, such as aluminum which gives the nose splint its rigidity. Conveniently, a central strip 32 is attached to layer 24 and is formed of the same resilient material as layer 24 and may be formed integrally with layer 24 or may be a separate strip which is adhesively attached to layer 24 just prior to use. The outer surface of strip 32 is coated with an adhesive 34 which carries an overlying protective paper backing 36 prior to use.

After adhesive strips 20 are placed firmly in place over the nose, as shown in FIG. 3, the paper backing strips 28 and 36 are removed from nose splint S. The nose splint is then placed with strip 32 pressed longitudinally along the bridge of the nose so that the adhesive surface 34 adheres to the nose to hold or press the incised tissue against the bone. The nose splint is then bent to conform to the shape of the nose as in FIG. 6 so that not only strip 32 but also layer 24 comes into adhesive contact with strips 20 over the incised area 14 and also extends beyond the incised area over the untreated tissue 19. Thus, the rigidity of the nose splint and the adhesive connection therebetween with the incised area of the nose as well as the untouched area, greatly minimizes any possible swelling of the incised tissue 14 or separation of this tissue from the adjacent bone and cartilage 16.

An alternative embodiment is shown in FIG. 7. In this embodiment the nose splint S' comprises a foam layer 38 which is tapered from the center to the outer edges, as shown. This foam layer may be made of the same material as foam layer 24 and is provided at the center with longitudinal parallel ridges 40 forming a trough 42 therebetween for fitting over the bridge of the nose as shown in FIG. 8. The embodiment of FIG. 7 includes adhesive material on the outer surface of layer 38 as in the previous embodiment, but has been omitted from the drawing for clarity of illustration. Also, the adhesive coating can be covered with a paper protective strip prior to use. The trough 42 is placed over the bridge of the nose and previously positioned adhesive strips 20 and is adhesively attached thereto and then the nose splint S' is bent around to conform to the shape of the nose and adhesively connected to strips 20 across the incised area 14 as well as the untreated tissue 19 whereupon the metal layer 14 holds or presses the tissue against the bone and cartilage 16 so that proper healing can take place as described above.

From the foregoing, the advantages of this invention are readily apparent. A nose splint has been provided which holds the incised tissue against the bone and cartilage during the healing process due to the adhesion between the relatively rigid splint and the incised and untreated skin by overlying adhesive strips 20. Thus, possible swelling of incised tissue 14 is minimized as is the flow of edema fluid 18 into the area between the incised skin and the bone and cartilage. In this way, the nose after healing is aesthetically appealing and does not encounter the problems which may occur if the incised skin is not held tightly against the bone and cartilage during the initial healing stages.

The invention has been described in detail with particular reference to a plurality of embodiments thereof, but it will be understood that variations and modifications can be effected within the spirit and scope of the invention.

I claim:

1. A splint for application to a traumatized nose of a human body to prevent swelling, including bones to be knitted together, said splint comprising:
    a base layer of thin, flexible, resilient material;
    a layer of adhesive on one side of said resilient material and adaptable to be adhesively secured to the traumatized portion;
    a layer of removable material overlying said adhesive layer prior to application of said splint to the traumatized nose of the human body to protect the adhesive layer; and
    a restraining layer of malleable metallic material attached permanently to the other side of said resilient material, said restraining layer being manually formable in situ to correspond to the shape of the traumatized portion and securable in place against the nose by said adhesive layer to minimize any swelling or change in the size and shape of the traumatized nose during recovery; and
    said base layer being thicker along an area adapted to overlie the bridge of a tramatized nose.

2. A splint, as claimed in claim 1, wherein said base layer comprises:
    a first portion of uniform thickness coextensive with said restraining component; and
    a second portion in the form of a strip overlying a central area of said first portion and adapted to overlie and engage the bridge of a traumatized nose so that upon forming said splint to the shape of the traumatized nose, said base layer substantially follows the contour of the nose so that substantially uniform pressure is applied to the nose.

3. A splint, as claimed in claim 1, wherein said base layer comprises:
    a thick midportion which tapers toward the outer edges;
    a pair of parallel ridges along said midportion with a trough therebetween so that upon forming said splint to the shape of the traumatized nose said base layer substantially follows the contour of the nose so that substantially uniform pressure is applied to the nose.

4. In a method of constructing the nose of a human being which includes the steps of fracturing the bone in the nose, incising the skin from the bone from a line along one side of the nose and across the bridge of the nose to a line along the opposite side of the nose, modifying the shape and construction of the nose, and applying a base layer of adhesive tape across the entire incised area and onto adjacent untreated tissue area to temporarily hold the nose in the desired shape, the improvement comprising:
    forming a splint having contiguous layers of resilient material and malleable metallic material and of a size to overlie the incised area as well as adjacent untreated tissue area;
    providing an adhesive surface on and co-extensive with said resilient material;
    applying the central portion of said splint adhesively to the bridge of the nose;
    pressing the side portions of the splint inwardly toward the sides of the nose to produce the desired shape and restraining effect by squeezing the edema fluid from between the incised skin and the bone; and
    adhesively adhering the splint to substantially the entire incised skin area to apply continuous pressure to hold the incised skin against the bone to minimize swelling so that the bones are not splayed apart.

* * * * *